(12) United States Patent
Yu et al.

(10) Patent No.: US 10,398,518 B2
(45) Date of Patent: Sep. 3, 2019

(54) ARTICULATING FLEXIBLE ENDOSCOPIC TOOL WITH ROLL CAPABILITIES

(71) Applicant: Auris Health, Inc., Redwood City, CA (US)

(72) Inventors: Alan Yu, Union City, CA (US); Jason Lee, Milpitas, CA (US)

(73) Assignee: Auris Health, Inc., Redwood City, CA (US)

( * ) Notice: Subject to any disclaimer, the term of this patent is extended or adjusted under 35 U.S.C. 154(b) by 204 days.

(21) Appl. No.: 15/388,955

(22) Filed: Dec. 22, 2016

(65) Prior Publication Data
US 2017/0100199 A1    Apr. 13, 2017

Related U.S. Application Data

(63) Continuation of application No. 15/072,072, filed on Mar. 16, 2016, now Pat. No. 9,561,083.
(Continued)

(51) Int. Cl.
| | |
|---|---|
| *A61B 34/30* | (2016.01) |
| *A61B 34/00* | (2016.01) |
| *A61B 1/005* | (2006.01) |
| *A61B 1/00* | (2006.01) |
| A61B 17/00 | (2006.01) |
| A61B 46/10 | (2016.01) |

(52) U.S. Cl.
CPC ............ *A61B 34/30* (2016.02); *A61B 1/0052* (2013.01); *A61B 1/0057* (2013.01); *A61B 1/00147* (2013.01); *A61B 34/71* (2016.02); *A61B 46/10* (2016.02); A61B 2017/0034 (2013.01); A61B 2017/00323 (2013.01); A61B 2034/301 (2016.02); A61B 2034/303 (2016.02)

(58) Field of Classification Search
CPC .......... A61B 34/30; A61B 2017/00323; A61B 2017/0034; A61B 2034/303; A61B 2034/301; A61B 1/0057; A61B 1/00147; A61B 1/0052; A61B 34/71; A61B 46/10
See application file for complete search history.

(56) References Cited

U.S. PATENT DOCUMENTS

| | | | |
|---|---|---|---|
| 2,556,601 | A | 6/1951 | Schofield |
| 2,566,183 | A | 8/1951 | Forss |

(Continued)

FOREIGN PATENT DOCUMENTS

| | | |
|---|---|---|
| CN | 101500470 | 8/2009 |
| CN | 102665590 | 9/2012 |

(Continued)

OTHER PUBLICATIONS

Notice of allowance dated Oct. 6, 2016 for U.S. Appl. No. 15/072,072.
(Continued)

*Primary Examiner* — Amber R Stiles
(74) *Attorney, Agent, or Firm* — Knobbe, Martens, Olson & Bear, LLP

(57) ABSTRACT

Instrument device with an elongated, flexible shaft that is configured to both roll and articulate in a controllable manner. The claimed system and apparatus provides endoscopic rolling and articulating capabilities with minimal tradeoffs in control, allowing for greater ease of use and clinical efficacy.

29 Claims, 14 Drawing Sheets

Related U.S. Application Data

(60) Provisional application No. 62/134,366, filed on Mar. 17, 2015.

(56) References Cited

U.S. PATENT DOCUMENTS

| | | |
|---|---|---|
| 2,730,699 A | 1/1956 | Gratian |
| 2,884,808 A | 5/1959 | Mueller |
| 3,294,183 A | 12/1966 | Riley et al. |
| 3,472,083 A | 10/1969 | Schnepel |
| 3,513,724 A | 5/1970 | Box |
| 3,572,325 A | 3/1971 | Bazell et al. |
| 3,595,074 A | 7/1971 | Johnson |
| 3,734,207 A | 5/1973 | Fishbein |
| 3,892,228 A | 7/1975 | Mitsui |
| 4,141,245 A | 2/1979 | Brandstetter |
| 4,241,884 A | 12/1980 | Lynch |
| 4,243,034 A | 1/1981 | Brandt |
| 4,351,493 A | 9/1982 | Sonnek |
| 4,357,843 A | 11/1982 | Peck et al. |
| 4,384,493 A | 5/1983 | Grunbaum |
| 4,507,026 A | 3/1985 | Lund |
| 4,530,471 A | 7/1985 | Inoue |
| 4,555,960 A | 12/1985 | King |
| 4,688,555 A | 8/1987 | Wardle |
| 4,741,326 A | 5/1988 | Sidall et al. |
| 4,745,908 A | 5/1988 | Wardle |
| 4,748,969 A | 6/1988 | Wardle |
| 4,784,150 A | 11/1988 | Voorhies et al. |
| 4,857,058 A | 8/1989 | Payton |
| 4,869,238 A | 9/1989 | Opie et al. |
| 4,907,168 A | 3/1990 | Boggs |
| 4,945,790 A | 8/1990 | Golden |
| 4,967,732 A | 11/1990 | Inoue |
| 5,050,585 A | 9/1991 | Takahashi |
| 5,106,387 A | 4/1992 | Kittrell et al. |
| 5,108,800 A | 4/1992 | Koo |
| 5,125,909 A | 6/1992 | Heimberger |
| 5,168,864 A | 12/1992 | Shockey |
| 5,207,128 A | 5/1993 | Albright |
| 5,234,428 A | 8/1993 | Kaufman |
| 5,256,150 A | 10/1993 | Quiachon et al. |
| 5,257,617 A | 11/1993 | Takahashi |
| 5,261,391 A | 11/1993 | Inoue |
| 5,277,085 A | 1/1994 | Tanimura et al. |
| 5,287,861 A | 2/1994 | Wilk |
| 5,313,934 A | 5/1994 | Wiita et al. |
| 5,350,101 A | 9/1994 | Godlewski |
| 5,386,818 A | 2/1995 | Schneebaum |
| 5,426,687 A | 6/1995 | Goodall et al. |
| 5,507,725 A | 4/1996 | Savage et al. |
| 5,524,180 A | 6/1996 | Wang et al. |
| 5,559,294 A | 9/1996 | Hoium et al. |
| 5,580,200 A | 12/1996 | Fullerton |
| 5,704,534 A | 1/1998 | Huitema et al. |
| 5,767,840 A | 6/1998 | Selker |
| 5,779,623 A | 7/1998 | Bonnell |
| 5,792,135 A | 8/1998 | Madhani et al. |
| 5,855,583 A | 1/1999 | Wang et al. |
| 5,873,817 A | 2/1999 | Kokish et al. |
| 5,876,325 A | 3/1999 | Mizuno et al. |
| 5,910,129 A | 6/1999 | Koblish et al. |
| 5,921,968 A | 7/1999 | Lampropoulos et al. |
| 5,938,586 A | 8/1999 | Wilk |
| 5,967,934 A | 10/1999 | Ishida et al. |
| 6,012,494 A | 1/2000 | Balazs |
| 6,084,371 A | 7/2000 | Kress et al. |
| 6,154,000 A | 11/2000 | Rastegar et al. |
| 6,157,853 A | 12/2000 | Blume et al. |
| 6,171,234 B1 | 1/2001 | White et al. |
| 6,185,478 B1 | 2/2001 | Koakutsu et al. |
| 6,198,974 B1 | 3/2001 | Webster, Jr. |
| 6,272,371 B1 | 8/2001 | Shlomo |
| 6,289,579 B1 | 9/2001 | Viza et al. |
| 6,315,715 B1 | 11/2001 | Taylor et al. |
| 6,394,998 B1 | 5/2002 | Wallace et al. |
| 6,401,572 B1 | 6/2002 | Provost |
| 6,404,497 B1 | 6/2002 | Backman |
| 6,436,107 B1 | 8/2002 | Wang et al. |
| 6,464,632 B1 | 10/2002 | Taylor |
| 6,487,940 B2 | 12/2002 | Hart et al. |
| 6,491,626 B1 | 12/2002 | Stone et al. |
| 6,491,701 B2 | 12/2002 | Tierney et al. |
| 6,537,205 B1 | 3/2003 | Smith |
| 6,554,793 B1 | 4/2003 | Pauker et al. |
| 6,695,818 B2 | 2/2004 | Wollschlager |
| 6,716,178 B1 | 4/2004 | Kilpatrick et al. |
| 6,726,675 B1 | 4/2004 | Beyar |
| 6,786,896 B1 | 9/2004 | Madhani et al. |
| 6,827,712 B2 | 12/2004 | Tovey et al. |
| 6,908,428 B2 | 6/2005 | Aizenfeld |
| 6,921,362 B2 | 7/2005 | Ouchi |
| 7,008,401 B2 | 3/2006 | Thompson et al. |
| 7,044,936 B2 | 5/2006 | Harding |
| 7,130,700 B2 | 10/2006 | Gardeski et al. |
| 7,172,580 B2 | 2/2007 | Hruska et al. |
| 7,276,044 B2 | 10/2007 | Ferry et al. |
| 7,615,042 B2 | 11/2009 | Beyar et al. |
| 7,635,342 B2 | 12/2009 | Ferry et al. |
| 7,645,230 B2 | 1/2010 | Mikkaichi |
| 7,766,856 B2 | 8/2010 | Ferry et al. |
| 7,771,416 B2 | 8/2010 | Spivey et al. |
| 7,789,874 B2 | 9/2010 | Yu et al. |
| 7,930,065 B2 | 4/2011 | Larkin et al. |
| 7,938,809 B2 | 5/2011 | Lampropoulos et al. |
| 7,974,674 B2 | 7/2011 | Hauck et al. |
| 7,998,020 B2 | 8/2011 | Kidd et al. |
| 8,052,636 B2 | 11/2011 | Moll et al. |
| 8,146,874 B2 | 4/2012 | Yu |
| 8,157,308 B2 | 4/2012 | Pedersen |
| 8,182,415 B2 | 5/2012 | Larkin et al. |
| 8,246,536 B2 | 8/2012 | Ochi |
| 8,291,791 B2 | 10/2012 | Light et al. |
| 8,444,637 B2 | 5/2013 | Podmore et al. |
| 8,498,691 B2 | 7/2013 | Moll et al. |
| 8,515,215 B2 | 8/2013 | Younge et al. |
| 8,746,252 B2 | 6/2014 | McGrogan et al. |
| 8,827,947 B2 | 9/2014 | Bosman et al. |
| 8,911,471 B2 | 12/2014 | Spivey et al. |
| 8,961,533 B2 | 2/2015 | Stahler et al. |
| 8,968,333 B2 | 3/2015 | Yu et al. |
| 9,173,713 B2 | 11/2015 | Hart et al. |
| 9,186,046 B2 | 11/2015 | Ramamurthy et al. |
| 9,204,933 B2 | 12/2015 | Reis et al. |
| 9,314,306 B2 | 4/2016 | Yu |
| 9,326,822 B2 | 5/2016 | Lewis et al. |
| 9,408,669 B2 | 8/2016 | Kokish et al. |
| 9,427,551 B2 | 8/2016 | Leeflang et al. |
| 9,452,018 B2 | 9/2016 | Yu |
| 9,457,168 B2 | 10/2016 | Moll et al. |
| 9,498,601 B2 | 11/2016 | Tanner et al. |
| 9,504,604 B2 | 11/2016 | Alvarez |
| 9,561,083 B2 | 2/2017 | Yu et al. |
| 9,566,201 B2 | 2/2017 | Yu |
| 9,591,990 B2 | 3/2017 | Chen et al. |
| 9,622,827 B2 | 4/2017 | Yu et al. |
| 9,636,184 B2 | 5/2017 | Lee et al. |
| 9,636,483 B2 | 5/2017 | Hart et al. |
| 9,668,814 B2 | 6/2017 | Kokish |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,818,681 B2 | 11/2017 | Machida |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 10,016,900 B1 | 7/2018 | Meyer et al. |

(56) References Cited

U.S. PATENT DOCUMENTS

| | | |
|---|---|---|
| 10,022,192 B1 | 7/2018 | Ummalaneni |
| 10,046,140 B2 | 8/2018 | Kokish et al. |
| 10,130,427 B2 | 11/2018 | Tanner et al. |
| 10,136,959 B2 | 11/2018 | Mintz et al. |
| 10,145,747 B1 | 12/2018 | Lin et al. |
| 10,159,532 B1 | 12/2018 | Ummalaneni et al. |
| 2001/0042643 A1 | 11/2001 | Krueger et al. |
| 2002/0045905 A1 | 4/2002 | Gerbi et al. |
| 2002/0098938 A1 | 7/2002 | Milbourne et al. |
| 2002/0117017 A1 | 8/2002 | Bernhardt et al. |
| 2002/0161355 A1 | 10/2002 | Wollschlager |
| 2002/0161426 A1 | 10/2002 | Lancea |
| 2002/0177789 A1 | 11/2002 | Ferry et al. |
| 2003/0158545 A1 | 8/2003 | Hovda et al. |
| 2003/0163199 A1 | 8/2003 | Chu et al. |
| 2003/0195664 A1 | 10/2003 | Nowlin et al. |
| 2004/0015053 A1 | 1/2004 | Bieger |
| 2004/0015122 A1 | 1/2004 | Zhang et al. |
| 2004/0138525 A1 | 7/2004 | Saadat et al. |
| 2004/0152972 A1 | 8/2004 | Hunter |
| 2004/0243147 A1 | 12/2004 | Lipow |
| 2005/0004515 A1 | 1/2005 | Hart et al. |
| 2005/0125005 A1 | 6/2005 | Fujikura |
| 2005/0154262 A1 | 7/2005 | Banik et al. |
| 2005/0159646 A1 | 7/2005 | Nordstrom et al. |
| 2005/0183532 A1 | 8/2005 | Najaf et al. |
| 2005/0222554 A1 | 10/2005 | Wallace et al. |
| 2005/0272975 A1 | 12/2005 | McWeeney et al. |
| 2005/0288549 A1 | 12/2005 | Mathis |
| 2006/0041188 A1 | 2/2006 | Dirusso et al. |
| 2006/0111692 A1 | 5/2006 | Hlavka et al. |
| 2006/0201688 A1 | 9/2006 | Jenner et al. |
| 2006/0237205 A1 | 10/2006 | Sia et al. |
| 2006/0264708 A1 | 11/2006 | Horne |
| 2006/0276827 A1 | 12/2006 | Mitelberg et al. |
| 2007/0000498 A1 | 1/2007 | Glynn et al. |
| 2007/0013336 A1 | 1/2007 | Nowlin et al. |
| 2007/0060879 A1 | 3/2007 | Weitzner et al. |
| 2007/0112355 A1 | 5/2007 | Salahieh |
| 2007/0135733 A1 | 6/2007 | Soukup et al. |
| 2007/0135763 A1 | 6/2007 | Musbach et al. |
| 2007/0149946 A1 | 6/2007 | Viswanathan |
| 2007/0156019 A1 | 7/2007 | Larkin et al. |
| 2007/0191177 A1 | 8/2007 | Nagai et al. |
| 2007/0245175 A1 | 10/2007 | Zheng et al. |
| 2007/0270645 A1 | 11/2007 | Ikeda |
| 2007/0270679 A1 | 11/2007 | Nguyen et al. |
| 2007/0282167 A1 | 12/2007 | Barenboym et al. |
| 2007/0287886 A1 | 12/2007 | Saadat |
| 2007/0299427 A1 | 12/2007 | Yeung et al. |
| 2008/0039255 A1* | 2/2008 | Jinno ............ A61B 17/062 474/148 |
| 2008/0046122 A1 | 2/2008 | Manzo et al. |
| 2008/0051629 A1 | 2/2008 | Sugiyama et al. |
| 2008/0065103 A1 | 3/2008 | Cooper et al. |
| 2008/0097293 A1 | 4/2008 | Chin et al. |
| 2008/0108869 A1 | 5/2008 | Sanders et al. |
| 2008/0139887 A1 | 6/2008 | Fitpatrick |
| 2008/0146874 A1 | 6/2008 | Miller |
| 2008/0147011 A1 | 6/2008 | Urmey |
| 2008/0177285 A1 | 7/2008 | Brock et al. |
| 2008/0208001 A1 | 8/2008 | Hadani |
| 2008/0212082 A1 | 9/2008 | Froggatt et al. |
| 2008/0214925 A1 | 9/2008 | Wilson et al. |
| 2008/0218770 A1 | 9/2008 | Moll et al. |
| 2008/0243064 A1* | 10/2008 | Stahler ............... A61B 34/71 604/95.01 |
| 2008/0245946 A1 | 10/2008 | Yu |
| 2008/0249536 A1 | 10/2008 | Stahler et al. |
| 2008/0253108 A1 | 10/2008 | Yu et al. |
| 2008/0262301 A1 | 10/2008 | Gibbons et al. |
| 2008/0302200 A1 | 12/2008 | Tobey |
| 2009/0082722 A1 | 3/2009 | Munger et al. |
| 2009/0098971 A1 | 4/2009 | Ho et al. |
| 2009/0099420 A1 | 4/2009 | Woodley et al. |
| 2009/0163851 A1 | 6/2009 | Holloway |
| 2009/0247880 A1 | 10/2009 | Naruse et al. |
| 2009/0247944 A1 | 10/2009 | Kirschenman et al. |
| 2009/0254083 A1 | 10/2009 | Wallace et al. |
| 2009/0262109 A1 | 10/2009 | Markowitz et al. |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0114115 A1 | 5/2010 | Schlesinger et al. |
| 2010/0130823 A1 | 5/2010 | Ando |
| 2010/0130987 A1 | 5/2010 | Wenderow et al. |
| 2010/0204646 A1 | 8/2010 | Plicchi et al. |
| 2010/0210923 A1 | 8/2010 | Li et al. |
| 2010/0248177 A1 | 9/2010 | Mangelberger et al. |
| 2011/0009863 A1 | 1/2011 | Stanislaw |
| 2011/0015484 A1 | 1/2011 | Alvarez et al. |
| 2011/0015648 A1 | 1/2011 | Alvarez et al. |
| 2011/0028991 A1 | 2/2011 | Ikeda et al. |
| 2011/0046441 A1 | 2/2011 | Wiltshire et al. |
| 2011/0077681 A1 | 3/2011 | Nagano |
| 2011/0098533 A1 | 4/2011 | Onoda |
| 2011/0130718 A1 | 6/2011 | Kidd et al. |
| 2011/0147030 A1 | 6/2011 | Blum et al. |
| 2011/0148442 A1 | 6/2011 | Berner |
| 2011/0152880 A1 | 6/2011 | Alvarez et al. |
| 2011/0238083 A1 | 9/2011 | Moll et al. |
| 2011/0261183 A1 | 10/2011 | Ma et al. |
| 2011/0277775 A1 | 11/2011 | Holop et al. |
| 2011/0288573 A1 | 11/2011 | Yates et al. |
| 2011/0306836 A1 | 12/2011 | Ohline et al. |
| 2012/0071821 A1 | 3/2012 | Yu |
| 2012/0071894 A1 | 3/2012 | Tanner et al. |
| 2012/0071895 A1 | 3/2012 | Stahler et al. |
| 2012/0123327 A1 | 5/2012 | Miller |
| 2012/0136419 A1 | 5/2012 | Zarembo et al. |
| 2012/0143226 A1 | 6/2012 | Belson et al. |
| 2012/0150154 A1 | 6/2012 | Brisson et al. |
| 2012/0186194 A1 | 7/2012 | Schlieper |
| 2012/0191107 A1 | 7/2012 | Tanner et al. |
| 2012/0239012 A1 | 9/2012 | Laurent et al. |
| 2012/0241576 A1 | 9/2012 | Yu |
| 2012/0259244 A1 | 10/2012 | Roberts et al. |
| 2012/0277730 A1 | 11/2012 | Salahieh |
| 2012/0283747 A1 | 11/2012 | Popovic |
| 2013/0018400 A1 | 1/2013 | Milton et al. |
| 2013/0030519 A1 | 1/2013 | Tran et al. |
| 2013/0035537 A1 | 2/2013 | Wallace et al. |
| 2013/0090552 A1 | 4/2013 | Ramamurthy et al. |
| 2013/0144116 A1 | 6/2013 | Cooper et al. |
| 2013/0165854 A1 | 6/2013 | Sandhu et al. |
| 2013/0165908 A1 | 6/2013 | Purdy et al. |
| 2013/0197556 A1 | 8/2013 | Shelton, IV et al. |
| 2013/0231678 A1 | 9/2013 | Wenderow |
| 2013/0269109 A1 | 10/2013 | Yu |
| 2013/0304084 A1 | 11/2013 | Beira et al. |
| 2013/0317276 A1 | 11/2013 | D'Andrea |
| 2013/0317519 A1 | 11/2013 | Romo et al. |
| 2013/0345519 A1 | 12/2013 | Piskun et al. |
| 2014/0000411 A1 | 1/2014 | Shelton, IV et al. |
| 2014/0046313 A1 | 2/2014 | Pederson et al. |
| 2014/0069437 A1 | 3/2014 | Reis et al. |
| 2014/0142591 A1 | 5/2014 | Alvarez et al. |
| 2014/0166023 A1 | 6/2014 | Kishi |
| 2014/0171778 A1 | 6/2014 | Tsusaka |
| 2014/0200402 A1 | 7/2014 | Snoke et al. |
| 2014/0222019 A1 | 8/2014 | Brudnick |
| 2014/0251042 A1 | 9/2014 | Asselin et al. |
| 2014/0276233 A1 | 9/2014 | Murphy |
| 2014/0276389 A1 | 9/2014 | Walker |
| 2014/0276391 A1 | 9/2014 | Yu |
| 2014/0276394 A1 | 9/2014 | Wong et al. |
| 2014/0276594 A1 | 9/2014 | Tanner et al. |
| 2014/0276647 A1 | 9/2014 | Yu |
| 2014/0276933 A1 | 9/2014 | Hart et al. |
| 2014/0276935 A1 | 9/2014 | Yu |
| 2014/0276936 A1 | 9/2014 | Kokish et al. |
| 2014/0276939 A1 | 9/2014 | Kokish et al. |
| 2014/0277333 A1 | 9/2014 | Lewis et al. |
| 2014/0277334 A1 | 9/2014 | Yu et al. |

(56) References Cited

U.S. PATENT DOCUMENTS

| | | |
|---|---|---|
| 2014/0309649 A1 | 10/2014 | Alvarez et al. |
| 2014/0316397 A1 | 10/2014 | Brown |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0032151 A1 | 1/2015 | Ishida et al. |
| 2015/0051592 A1 | 2/2015 | Kintz |
| 2015/0090063 A1 | 4/2015 | Lantermann et al. |
| 2015/0101442 A1 | 4/2015 | Romo |
| 2015/0119638 A1 | 4/2015 | Yu et al. |
| 2015/0133963 A1 | 5/2015 | Barbagli |
| 2015/0142013 A1 | 5/2015 | Tanner et al. |
| 2015/0148600 A1 | 5/2015 | Ashinuma et al. |
| 2015/0164594 A1 | 6/2015 | Romo et al. |
| 2015/0164596 A1 | 6/2015 | Romo |
| 2015/0182250 A1 | 7/2015 | Conlon et al. |
| 2015/0231364 A1 | 8/2015 | Blanchard |
| 2015/0327939 A1 | 11/2015 | Kokish et al. |
| 2015/0335480 A1 | 11/2015 | Alvarez et al. |
| 2015/0374445 A1 | 12/2015 | Gombert et al. |
| 2016/0001038 A1 | 1/2016 | Romo et al. |
| 2016/0007881 A1 | 1/2016 | Wong et al. |
| 2016/0067450 A1 | 3/2016 | Kowshik |
| 2016/0100896 A1 | 4/2016 | Yu |
| 2016/0151122 A1 | 6/2016 | Alvarez et al. |
| 2016/0166234 A1 | 6/2016 | Zhang |
| 2016/0235946 A1 | 8/2016 | Lewis et al. |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0296294 A1 | 10/2016 | Moll et al. |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2016/0354582 A1 | 12/2016 | Yu et al. |
| 2016/0374541 A1 | 12/2016 | Agrawal et al. |
| 2016/0374590 A1 | 12/2016 | Wong et al. |
| 2017/0007337 A1 | 1/2017 | Dan |
| 2017/0007343 A1 | 1/2017 | Yu |
| 2017/0065364 A1 | 3/2017 | Schuh et al. |
| 2017/0065365 A1 | 3/2017 | Schuh |
| 2017/0071684 A1 | 3/2017 | Kokish et al. |
| 2017/0105804 A1 | 4/2017 | Yu |
| 2017/0119413 A1 | 5/2017 | Romo |
| 2017/0119481 A1 | 5/2017 | Romo et al. |
| 2017/0119484 A1 | 5/2017 | Tanner et al. |
| 2017/0151028 A1 | 6/2017 | Ogawa et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209672 A1 | 7/2017 | Hart et al. |
| 2017/0252540 A1 | 9/2017 | Weitzner et al. |
| 2017/0290631 A1 | 10/2017 | Lee et al. |
| 2017/0296784 A1 | 10/2017 | Kokish |
| 2017/0312481 A1 | 11/2017 | Covington et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0042464 A1 | 2/2018 | Arai |
| 2018/0049792 A1 | 2/2018 | Eckert |
| 2018/0055589 A1 | 3/2018 | Joseph et al. |
| 2018/0056044 A1 | 3/2018 | Choi et al. |
| 2018/0177383 A1 | 6/2018 | Noonan et al. |
| 2018/0177556 A1 | 6/2018 | Noonan et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0296299 A1 | 10/2018 | Iceman |
| 2018/0325499 A1 | 11/2018 | Landey et al. |
| 2018/0326181 A1 | 11/2018 | Kokish et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |

FOREIGN PATENT DOCUMENTS

| | | | |
|---|---|---|---|
| DE | 19649082 | 1/1998 | |
| DE | 102004020465 | 9/2005 | |
| EP | 0 543 539 | 5/1993 | |
| EP | 0 776 739 | 6/1997 | |
| EP | 1 442 720 | 8/2004 | |
| EP | 0 904 796 | 11/2004 | |
| EP | 3 025 630 | 6/2016 | |
| JP | 2006-525087 | 11/2006 | |
| JP | 2007-511247 | 5/2007 | |
| JP | 2009-139187 | 6/2009 | |
| JP | 2010-046384 | 3/2010 | |
| JP | 2011-015992 | 1/2011 | |
| WO | WO 94/14494 | 7/1994 | |
| WO | WO 00/67640 | 11/2000 | |
| WO | WO 02/074178 | 9/2002 | |
| WO | WO 02074178 A2 * | 9/2002 | ............ A61B 90/36 |
| WO | WO 04/039273 | 5/2004 | |
| WO | WO 04/105849 | 12/2004 | |
| WO | WO 05/032637 | 4/2005 | |
| WO | WO 05/081202 | 9/2005 | |
| WO | WO 09/097461 | 6/2007 | |
| WO | WO 08/097540 | 8/2008 | |
| WO | WO 09/092059 | 7/2009 | |
| WO | WO 10/081187 | 7/2010 | |
| WO | WO 10/088187 | 8/2010 | |
| WO | WO 11/005335 | 1/2011 | |
| WO | WO 13/179600 | 12/2013 | |
| WO | WO 15/093602 | 12/2013 | |
| WO | WO 15/127231 | 8/2015 | |
| WO | WO 16/003052 | 1/2016 | |

OTHER PUBLICATIONS

Office action dated Jun. 15, 2016 for U.S. Appl. No. 15/072,072.
Mayo Clinic, Robotic Surgery, https://www.mayoclinic.org/tests-procedures/robotic-surgery/about/pac-20394974?p=1, downloaded from the internet on Jul. 12, 2018, 2 pp.

* cited by examiner

ARTICULATING FLEXIBLE ENDOSCOPIC TOOL WITH ROLL CAPABILITIES

CROSS-REFERENCE

This application is a continuation of U.S. patent application Ser. No. 15/072,072, filed Mar. 16, 2016, which claims the benefit of U.S. Provisional Application No. 62/134,366, filed Mar. 17, 2015, which applications are incorporated herein by reference.

The present invention relates to medical instruments, tools, and methods that may be incorporated into a robotic system, such as those disclosed in U.S. patent application Ser. No. 14/523,760, filed Oct. 24, 2014, U.S. Provisional Patent Application No. 62/019,816, filed Jul. 1, 2014, U.S. Provisional Patent Application No. 62/037,520, filed Aug. 14, 2014, and U.S. Provisional Patent Application No. 62/057,936, filed Sep. 30, 2014, the entire contents of which are incorporated herein by reference.

BACKGROUND OF THE INVENTION

1. Field of the Invention

The field of the present invention relates to flexible endoscopic tools that may be used in a number of endolumenal procedures. More particularly, the field of the invention pertains to flexible endoscopic tools that have roll capabilities for use during endolumenal procedures.

2. Description of the Background Art

The spread of robotic surgery has precipitated the development of novel technologies. For example, in order to enable robotically-driven endoscopes, robotically-driven tools are more useful when they are able to both articulate in a desired linear direction and roll in a desired angular direction. In current elongated medical devices, roll in the device shafts is often achieved at the expense of pull-cable management. For example, in some laparoscopic devices on the market, roll of the rigid shaft may be accomplished by simply twisting the actuation pull wires (used for manipulation of the device's end effectors and/or wrist) around each other at the same rate as the shaft. Due to mechanically-limited revolutions in either direction, the twist in the cables show little to no adverse effect on either roll or grasper manipulation. Nevertheless, this lack of pull-wire management results in noticeably varying levels of friction throughout the shaft rotations. The accumulated friction steadily increases with each rotation until the pull wires are tightly bound around one another.

FIG. 1 illustrates the physical limitations of current elongated devices arising from the implementation of roll capabilities. Specifically, FIG. 1 illustrates how the implementation of roll capabilities in a prior art device creates undesirable friction and winding of the articulation pull wires. As shown in FIG. 1, the pull wires 104 in prior art device 100 extend from the distal tip 102 and at the proximal end 101 of the device 100. Rotation of the shaft 103 forces the pull wires 104 to twist amongst one another along the entire length of the hollow shaft 103. As the shaft 103 rotates beyond a full rotation, the tensioned wires start to tightly wrap around one another much like a wire-rope. Eventually, the pull-wires 104 would not be able to overcome the resulting friction to exert tension on the elements on the distal end 102.

In competing products, such as the TransEnterix SurgiBot, articulation and roll are de-coupled using a robotic outer "sheath" to enable pitch and yaw articulation, while a flexible laparoscopic tool controls insertion roll and end-effector actuation. However, this results in an unnecessarily large system with two separate modules controlling different degrees of freedom. Separate modules complicate the pre-operative workflow because the operator must now register two sets of devices relative to the patient.

In manual endoscopes, knobs and dials actuate the distal tip of the scope while rotation of the shaft is achieved by twisting the entire proximal end of the tool. As a result, when rolling the scope, the operator is forced to contort into an uncomfortable, compensatory position in order to operate the knobs and dials. These contortions are undesirable; thus, necessitating a different approach.

Accordingly, there is a need for an endoscopic tool that is capable of rolling without compromise to its actuation and articulation capabilities, while also being ergonomically ease to use.

SUMMARY OF THE INVENTION

In general, the present invention provides a flexible endoscopic tool that has both articulation and roll capabilities. In one aspect, the present invention provides for a medical instrument comprising an elongated member, and an instrument base located at the proximal end of the elongated member, the base comprising a pull wire configured to spiral along the shaft at a helical pitch and a helical angle, and a translating redirect member configured to direct the pull wire to begin spiraling along the elongated member at a consistent angular position on the elongated member.

In another aspect, the instrument base further comprises a lead screw configured to longitudinally translate the redirect member relative to the elongated member in response to rotating the lead screw. In another aspect, the lead screw is further configured to roll the elongated member. In another aspect, longitudinal translation of the redirect member relative to the shaft maintains the helical pitch of the pull wire around the shaft it rolls. In another aspect, longitudinal translation of the redirect member relative to the shaft maintains the helical angle of the pull wire around the shaft it rolls.

In yet another aspect, the medical instrument further comprises a rotatable spool configured to rotate in response to longitudinal translation by the redirect member. In another aspect, the spool rotates in order to either collect or pull wire length. In another aspect, the lead screw is coupled to a transmission gear that is configured to transmit angular motion from the lead screw to the elongated member.

BRIEF DESCRIPTION OF THE DRAWINGS

The invention will be described, by way of example, and with reference to the accompanying diagrammatic drawings, in which.

DETAILED DESCRIPTION OF THE INVENTION

Although certain preferred embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

In clinical applications, the design of the instrument base, which includes the robotic interface and the mechanical assembly to enable articulation and roll, is often constrained in size and design. For example, in a robotically-driven system, the design of the instrument base may be limited by both the lifting power of the robotic appendages and the necessity of maintaining a sterile barrier. Moreover, the use of pull wires to actuate the endoscopic shaft further complicates attempts to implement roll into the endoscopic shaft design.

Accordingly, the present invention provides an efficient, compact design for a robotically-driven tool that accomplishes both articulation and roll in its shaft with minimal design compromises.

Figure 1:
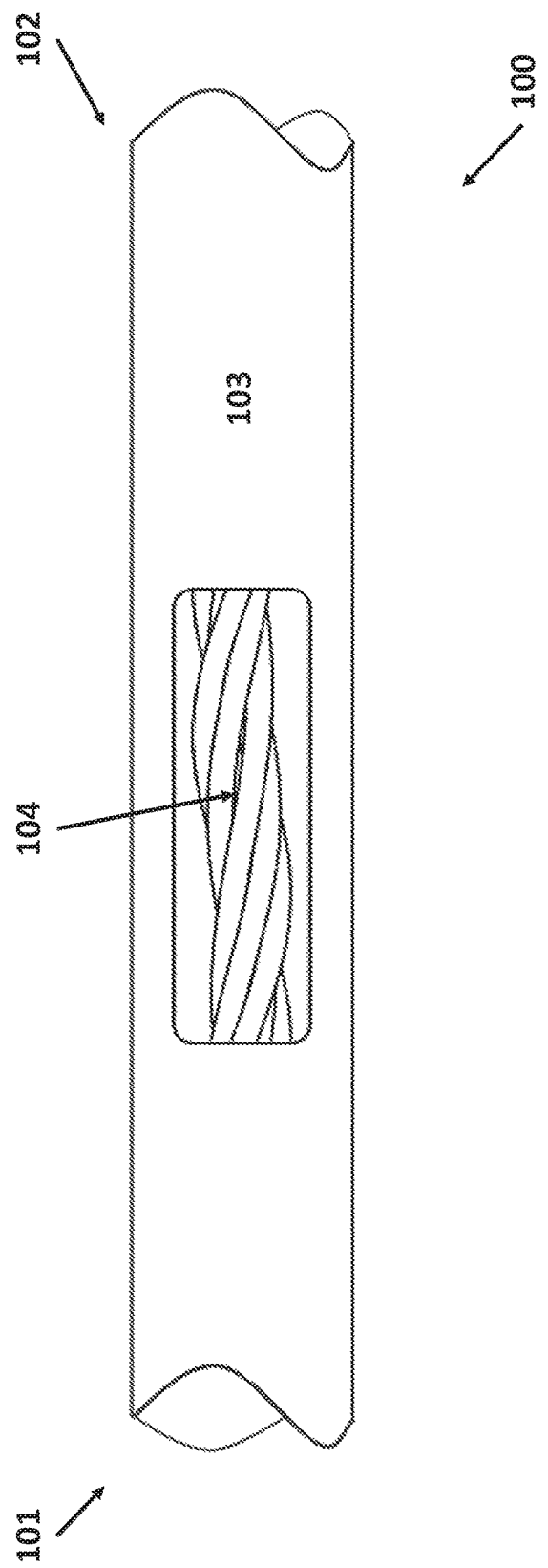
FIG. 1 illustrates the physical limitations in current elongated devices arising from the implementation of roll capabilities, consistent with the current state of the art.
Figure 2A:
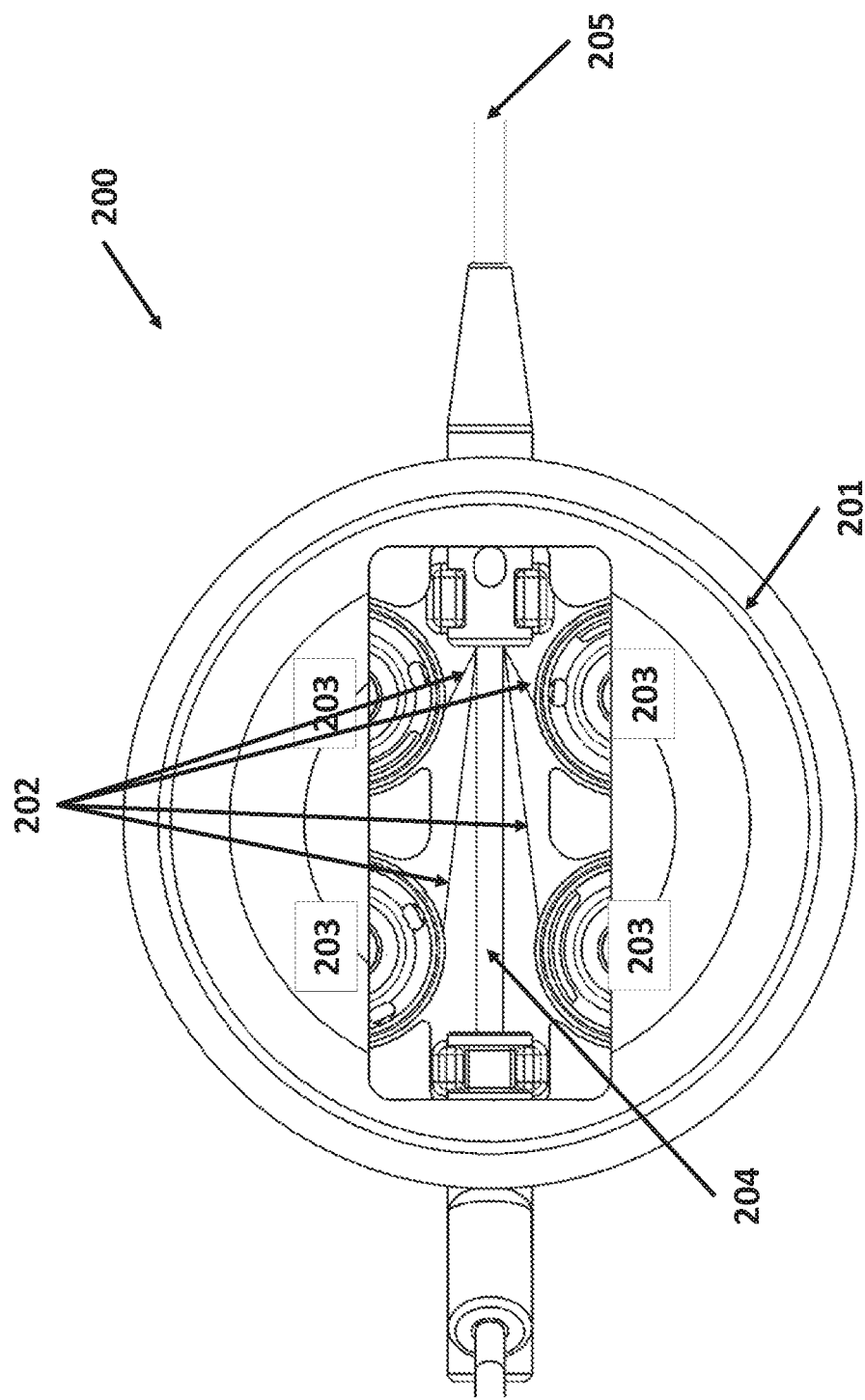
FIGS. 2A-2C illustrates the physical limitations arising from use of a central shaft to capture the winding pull wires arising from rotations, in accordance with an embodiment of the present invention.
Figure 2B:
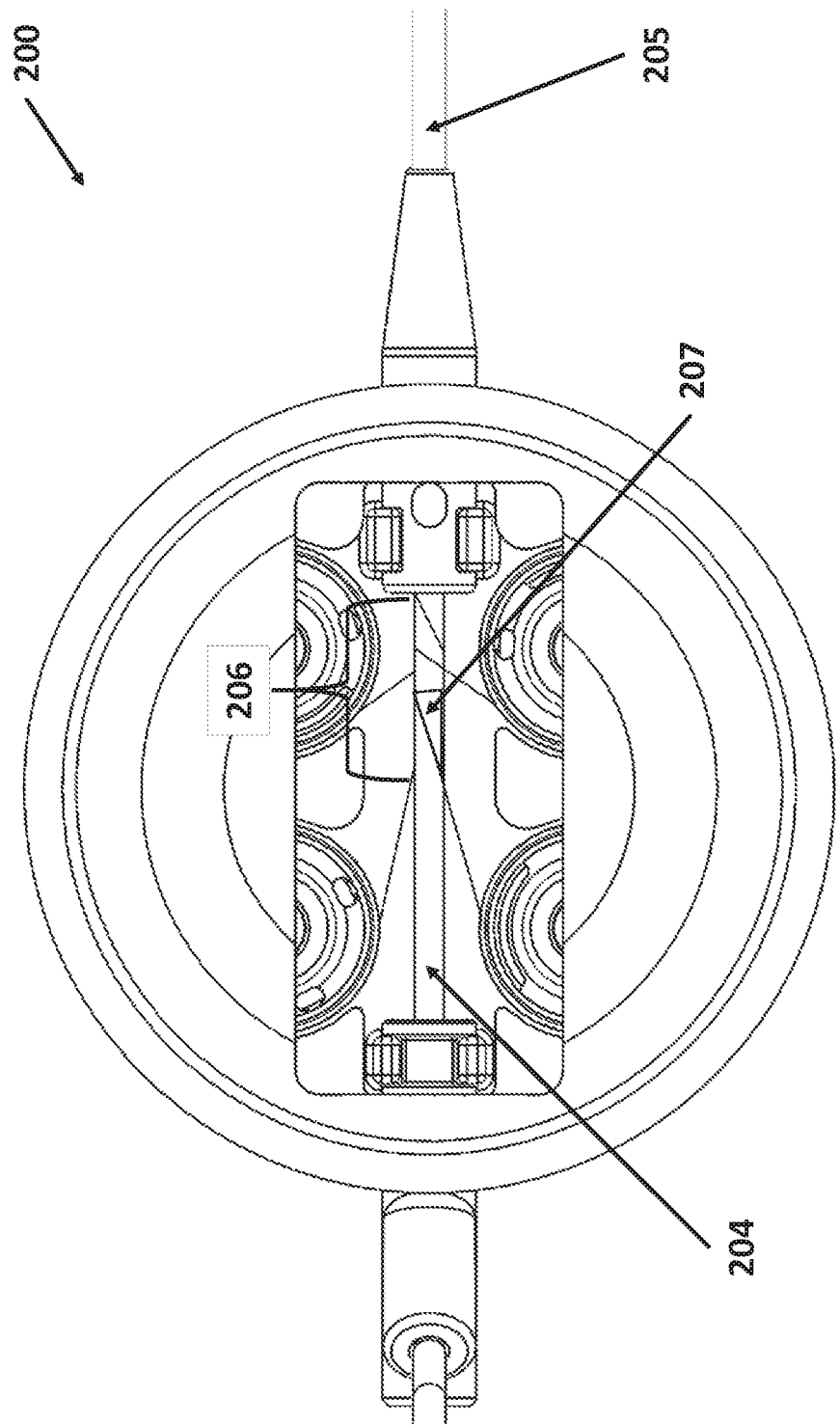
Figure 2C:
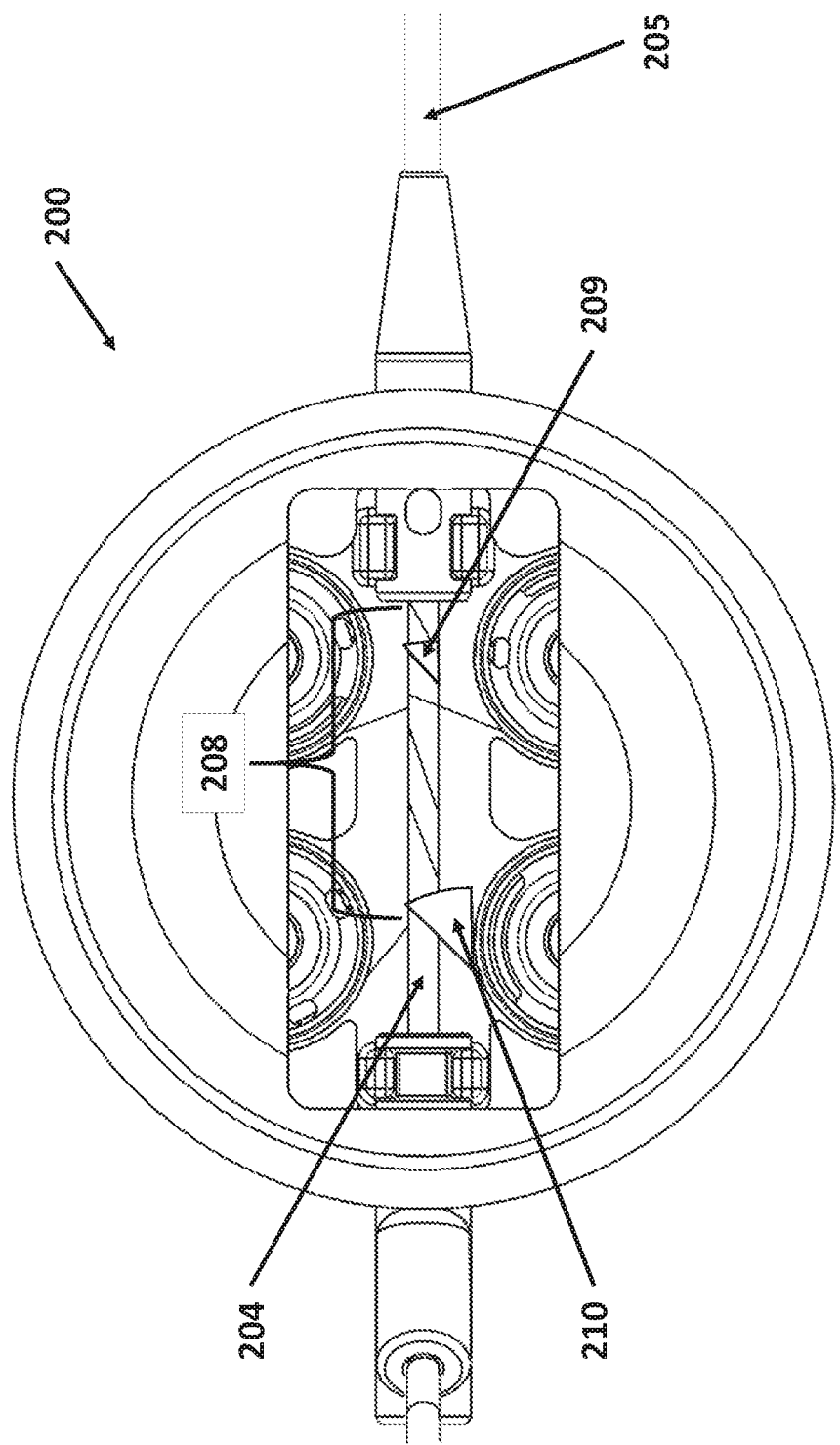

An improvement on current devices, use of an internal shaft within the elongated shaft may be used to interrupt the wire-on-wire wrapping by introducing a low-friction surface upon which the wire can wrap around. Merely adding an internal shaft to the current art, however, creates a number of engineering challenges. FIGS. 2A-2C illustrates the physical limitations arising from use of a central shaft to capture the winding pull wires arising from rotations, in accordance with an embodiment of the present invention. In FIG. 2A, the device 200 remains at rest with respect to roll, revealing that the pull wires 202 within the instrument base 201 in device 200 extend from the spools 203 to the distal end of the internal shaft 204. The outer shaft 205 is configured with a concentrically aligned internal shaft 204 that is designed to act as a low-friction surface upon which the wires may wrap around.

In FIG. 2B, the outer shaft 205 has been slightly rotated, resulting in the pull wires 202 winding around the internal shaft 204. The pull wire 202 winding and twisting around internal shaft 204 results in the pull wires 202 spiraling into a wrap 206 around the internal shaft 204 at particular helical angle 207 and helical pitch as the outer shaft 205 rolls.

In FIG. 2C, the outer shaft 205 has been heavily rotated, resulting the pull wires 202 further winding around the internal shaft 204. As the outer shaft 205 is rotated, the pull wires 202 "crawl" along the internal shaft 204 in order to compensate for their changed angular position with respect to the internal shaft 204. The resulting wrap 208 of the pull wires 202, however, causes the helical angle 209 of the wrap 208 to grow progressively aggressive, i.e., the helical angles of the wrap 208 grow steeper and steeper relative to the internal shaft 204.

The change in the helical angles of wrap 208 are largely the result of the changing "takeoff angle" 210, i.e., the angle at which the pull wires 202 begin to wrap around the internal shaft 204, as the external shaft 205 rolls. As the internal shaft 204 rotates, the static position of the spools 202 relative to internal shaft 204 and wrap 208 creates a steeper and steeper takeoff angle 210 as the wrap 208 crawls along the internal shaft 204. Additionally, since the spools are at different locations relative to the wrap 208, the takeoff angles at each spool may be different. At the extreme, the wrap 208 around the internal shaft 204 would lock due to friction, a phenomenon that reflects Capstan's principle, wherein the helical pitch 209 would be orthogonal to the internal shaft 204, resulting in the wrap 208 completely wrapping about itself, i.e., where the helical pitch would be zero. At that point, the pull-wire 202 would not be able to overcome the friction and serve its purpose.

The "crawl" of the wrap 208 also transmits tension in the pull wires 202. When pull wires are used in flexible devices, such as catheters, the resulting tension from roll is undesirable and can lead to shaft compression, unwanted stiffness, and hindered steering performance. Moreover, the resulting tension is non-linear and unpredictable, leading to an unpredictable mathematical model for controlling the device. Given that a changing helical angle and helical pitch creates controls and engineering challenges, additional embodiments are needed that incorporate internal shaft roll mechanisms to accommodate.

Figure 3:
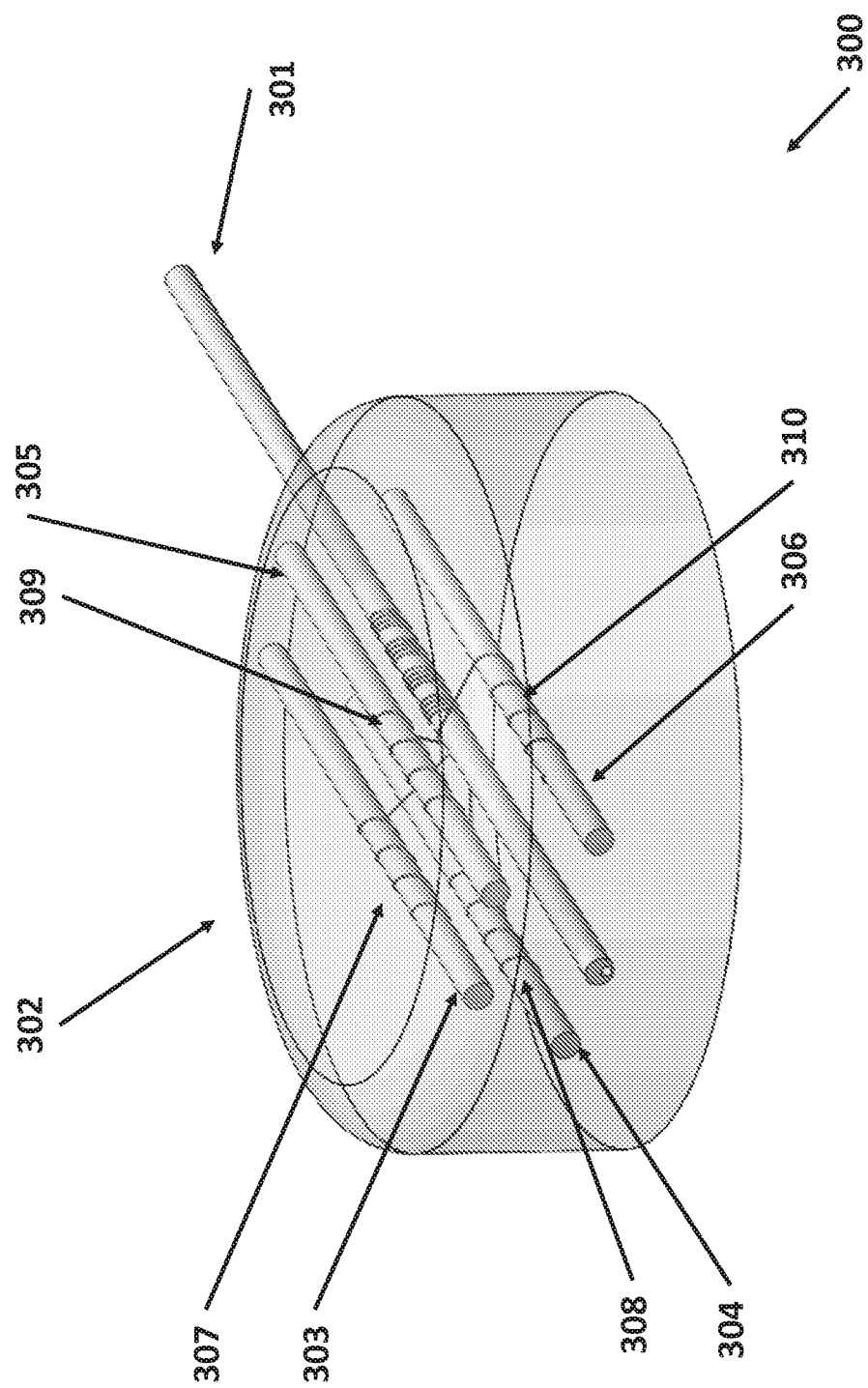
FIG. 3 illustrates an endoscopic device with an instrument base comprising multiple rolling structures, in accordance with an embodiment of the present invention.

FIG. 3 illustrates an endoscopic device with an instrument base comprising multiple rolling structures, in accordance with an embodiment of the present invention. In FIG. 3, the device 300 comprises an elongated shaft 301 and instrument base 302. The instrument base 302 comprises four articulation shafts 303, 304, 305, and 306 that act as redirect surfaces for pull wires 307, 308, 309, and 310 respectively. Each of the aforementioned pull wires are wrapped in spiral fashion around their respective articulation shafts before being wrapped in spiral fashion around the elongated shaft 301.

Figure 4A:
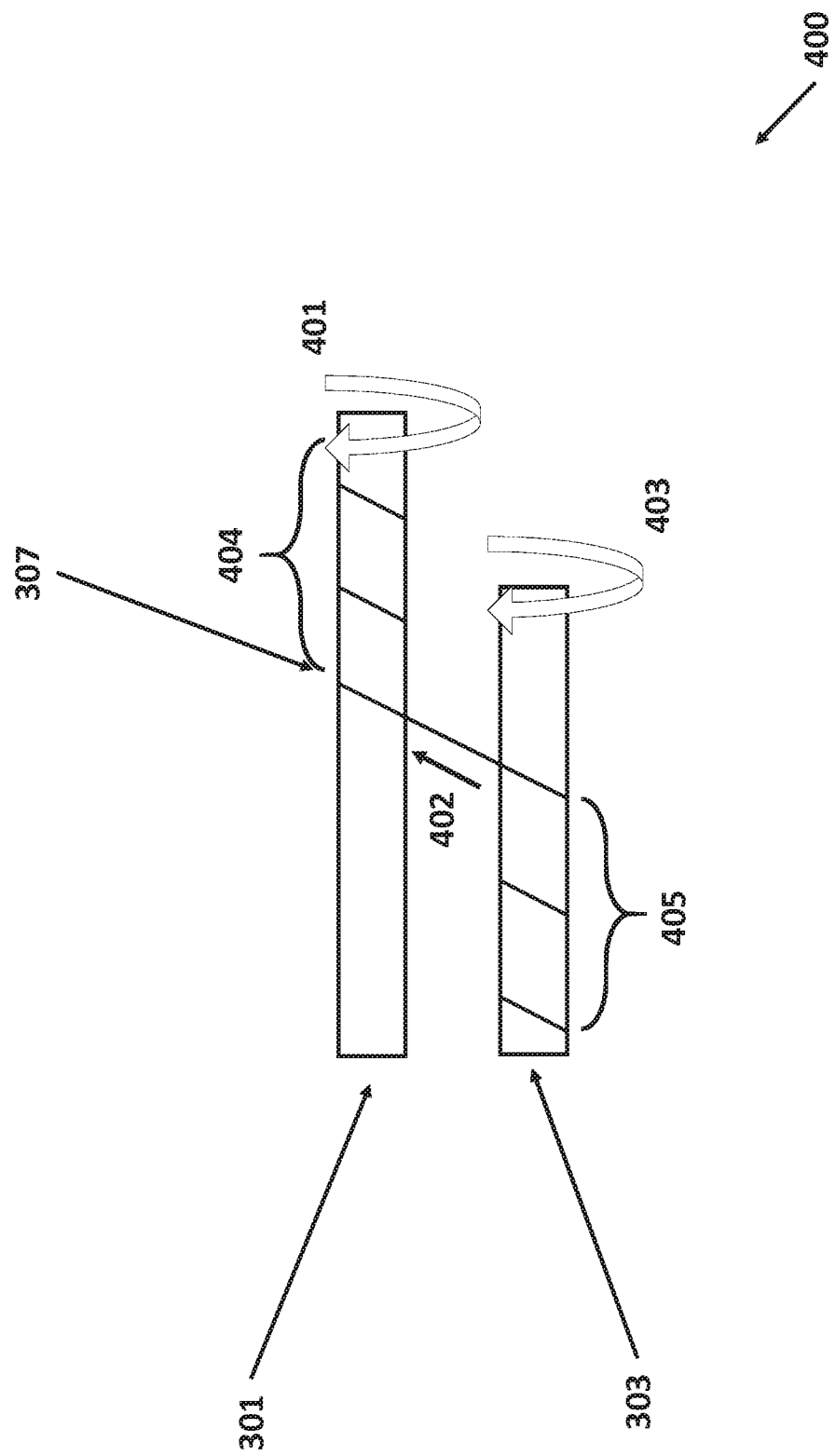
FIGS. 4A-4B illustrates how the helical angle of the pull wire wrap around the elongated shaft may be controlled by rolling the articulation shaft in concert with rolling the elongated shaft, in accordance with an embodiment of the present invention.
Figure 4B:
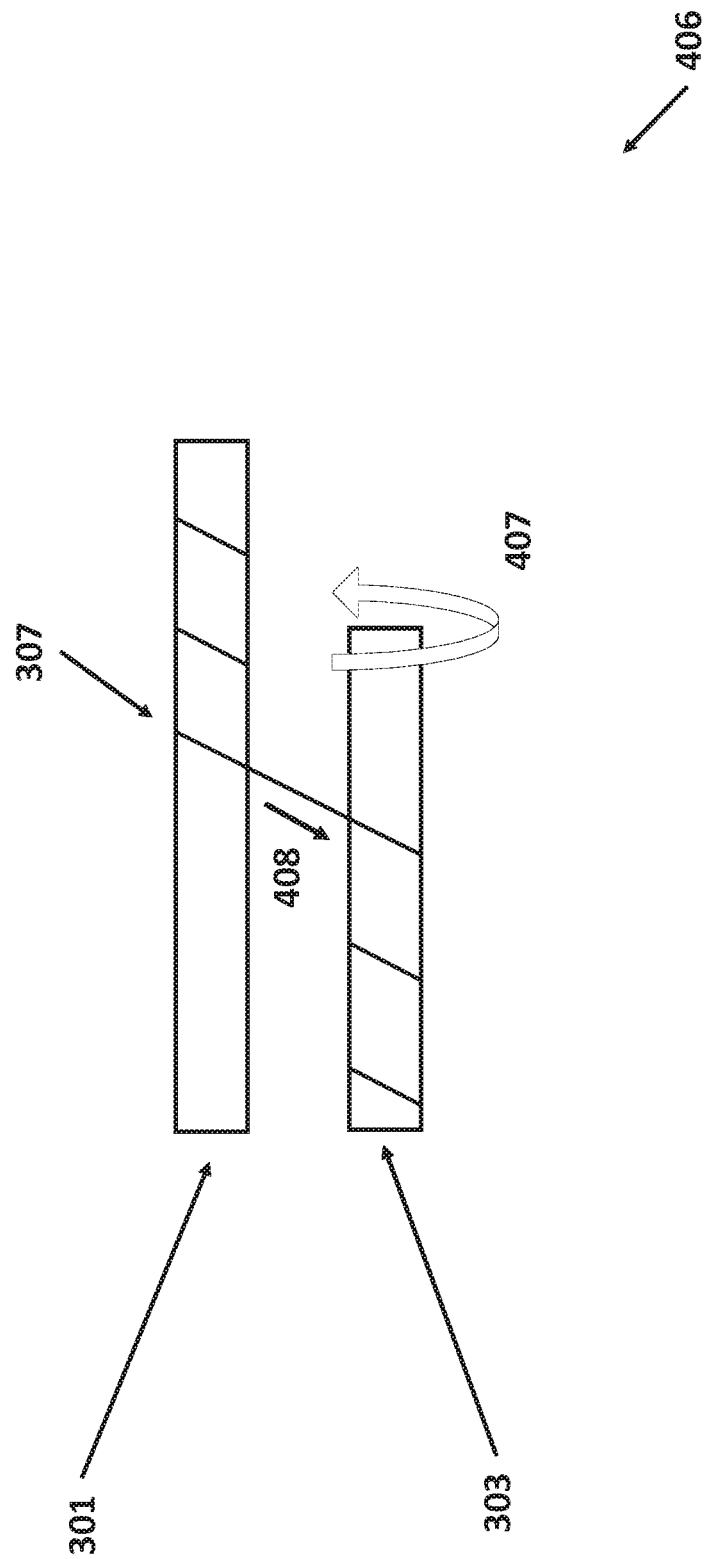

The use of parallel articulation shafts provides for controlled wrapping of the pull wires around the elongated shaft due to roll by coordinating roll among the articulation shafts. FIGS. 4A-4B illustrates how the helical angle of the pull wire wrap around the elongated shaft may be controlled by rolling the articulation shaft in concert with rolling the elongated shaft, in accordance with an embodiment of the present invention. Specifically, FIG. 4A illustrates how roll of the elongated shaft 301 from device 300 may be accomplished without creating an unstable helical pitch and angle and undesirable tension. In FIG. 4A, view 400 isolates and focuses on pull wire 307 wrapped around both articulation shaft 303 and elongated shaft 301 within instrument base 302 of device 300 from FIG. 3. When elongated shaft 301 is rolled in the direction shown by arrow 401, in the absence of any corresponding roll in articulation shaft 303, undesirable tension 402 would result in pull wire 307. Accordingly, to compensate for that rise in tension 402, articulation shaft 303 may be rolled in the (same) direction as the elongated shaft 301 as shown by arrow 403. In effect, as the elongated shaft 301 "wraps" up the pull wire 307, additional length of pull wire 307 is "unwrapped" from articulation shaft 303. When the rate of roll 401 and 403 are matched, there is no tension or slack in the pull wire 307. This ensures that the helical pitch and angle of the wrap 404 on elongated shaft 301 and the helical pitch and angle of the wrap 405 on the articulation shaft 303 is consistent and predictable. This results in a linear mathematical model for calculating control of the pull wire 307.

FIG. 4B illustrates how tension on pull wire 307 may be generated by rolling the articulation shaft 303 relative to the elongated shaft 301, in accordance with an embodiment of the present invention. In FIG. 4B, view 406 shows rotation of the articulation shaft 303 in the direction indicated by arrow 407. If elongated shaft 301 rolls at a slower rate in the same direction, rolls in the opposite direction, or is held in place rotationally, pull wire 307 will experience tension in the direction indicated by arrow 408. Accordingly, tension along the pull wire 307 conveys axial compression force down the elongated shaft 301 of the device, resulting in articulation of the device. In circumstances when used in combination with an end effector, the axial compression results in actuation of the end effector element.

As shown in FIGS. 4A and 4B, providing secondary structures that assist with the wrap may accommodate the wrapping of the pull wires around the central shaft. The coordinated rolling of both the elongated shaft 301 in combination with the articulation shaft 303, which wraps pull wires at a precise helical pitch and angle, allows for a consistent helical pitch and angle on the elongated shaft 301, regardless of whether the operator desires roll in the elongated shaft 301 or tension in the pull wires. In practice, maintaining a consistent helical pitch generally results in a consistent helical angle.

While embodiments with multiple rolling structures resolve several of the design challenges arising from incorporating articulation and roll, in practice, the use of multiple rolling structures may create issues when attempting to interface the instrument with the robotic drive mechanism.

Figure 5A:
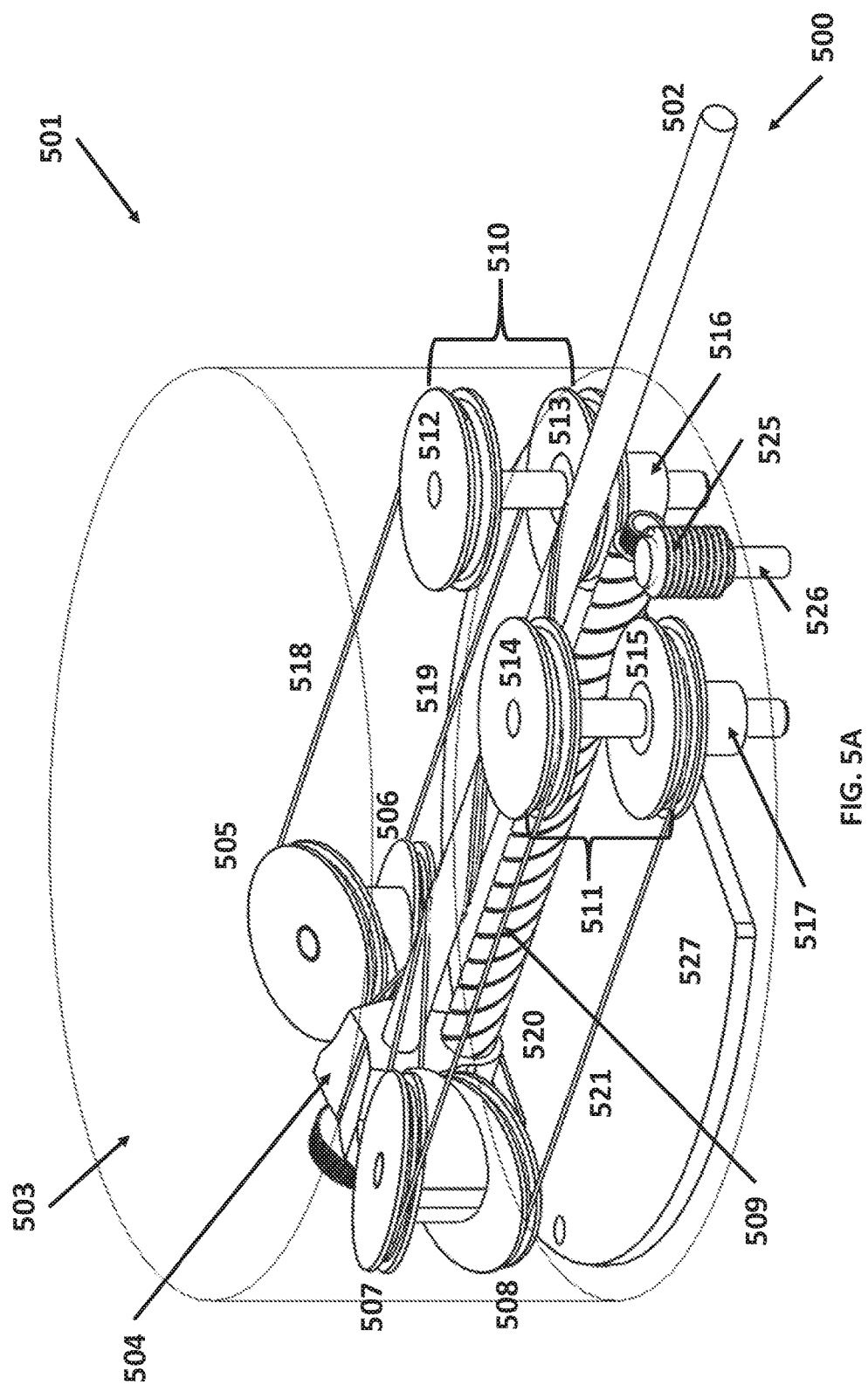
FIG. 5A illustrates an endoscopic device with an instrument base that utilizes a lead screw and angled idlers to ensure a consistent helical pitch around an elongated shaft, in accordance with an embodiment of the present invention.

FIG. 5A illustrates an endoscopic device with an instrument base that utilizes a lead screw and angled idlers to ensure a consistent helical angle and pitch around an elongated shaft, in accordance with an embodiment of the present invention. As shown in isometric transparent view 500, endoscopic device 501 principally comprises an elongated shaft 502 and an instrument base 503. Within instrument base 503, an idler carriage 504 is disposed along the elongated shaft 502, and configured to longitudinally translate and slide along the elongated shaft 502.

Figure 5B:
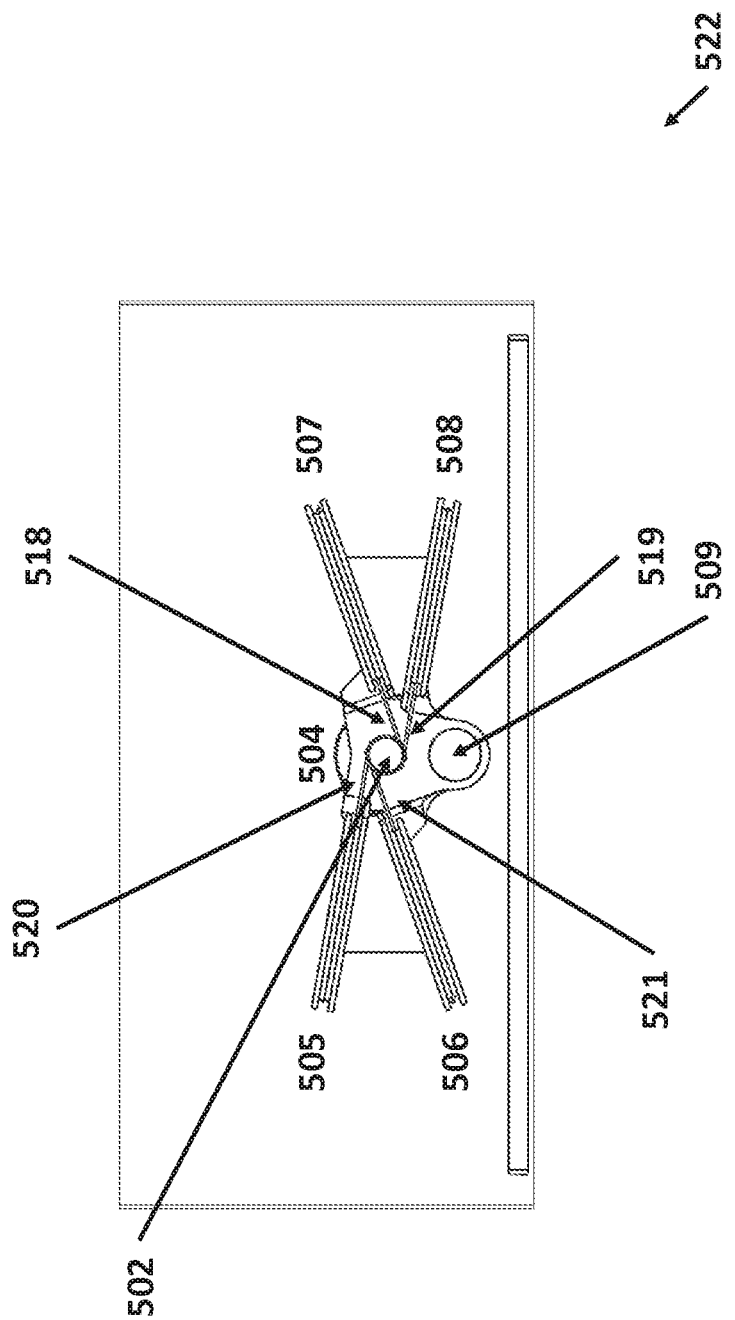
FIG. 5B illustrates a frontal view of idler carriage 504 and elongated shaft 502 in endoscopic device 501 from FIG. 5A.

The idler carriage 504 holds four angled idlers 505, 506, 507, and 508 at a fixed angle relative to the elongated shaft 502. The angle of the angled idlers may be chosen for a particular purpose. FIG. 5B illustrates a frontal view of idler carriage 504 and elongated shaft 502 in endoscopic device 501 from FIG. 5A. In FIG. 5B, cross-sectional frontal view 522 shows how the idler carriage 504 positions angled idlers 505, 506, 507, and 508 deliver the pull wires 518, 519, 520, and 521 to the elongated shaft 502 at a consistent and predictable location. In contrast to the previously disclosed embodiments, the angled idlers in endoscopic device 501 wrap and un-wrap the pull wires at the same longitudinal position along the elongated shaft 502, which assists in maintaining a consistent takeoff angle for all of the pull wires regardless of the length of pull wire wrap around shaft 502.

As shown in FIG. 5A, the instrument base 503 also incorporates a pair of rotating structures 510 and 511. Rotating structures 510 and 511 comprise two concentrically-aligned, co-radial spools, such as spools 512, 513 from rotating structure 510, and spools 514, 515 from rotating structure 511. The rotating structures 510 and 511 incorporate output shafts 516 and 517 that interface with robotic drive and control mechanisms. Given that spools 512 and 513 and spools 514 and 515 are co-radial, output shaft 516 and 517 each includes both an inner and outer sub-shaft that drives each spool per rotating structure.

In some embodiments, the output shafts may be replaced by "female" or receiving interfaces rather "male" or protruding interfaces. As shown in isometric view 500, pull wires 518, 519, 520, and 521 are coiled around spools 512, 513, 514, and 515 and run around the angled idlers 505, 506, 507, and 508 before spiraling around the elongated shaft 502.

Figure 5C:
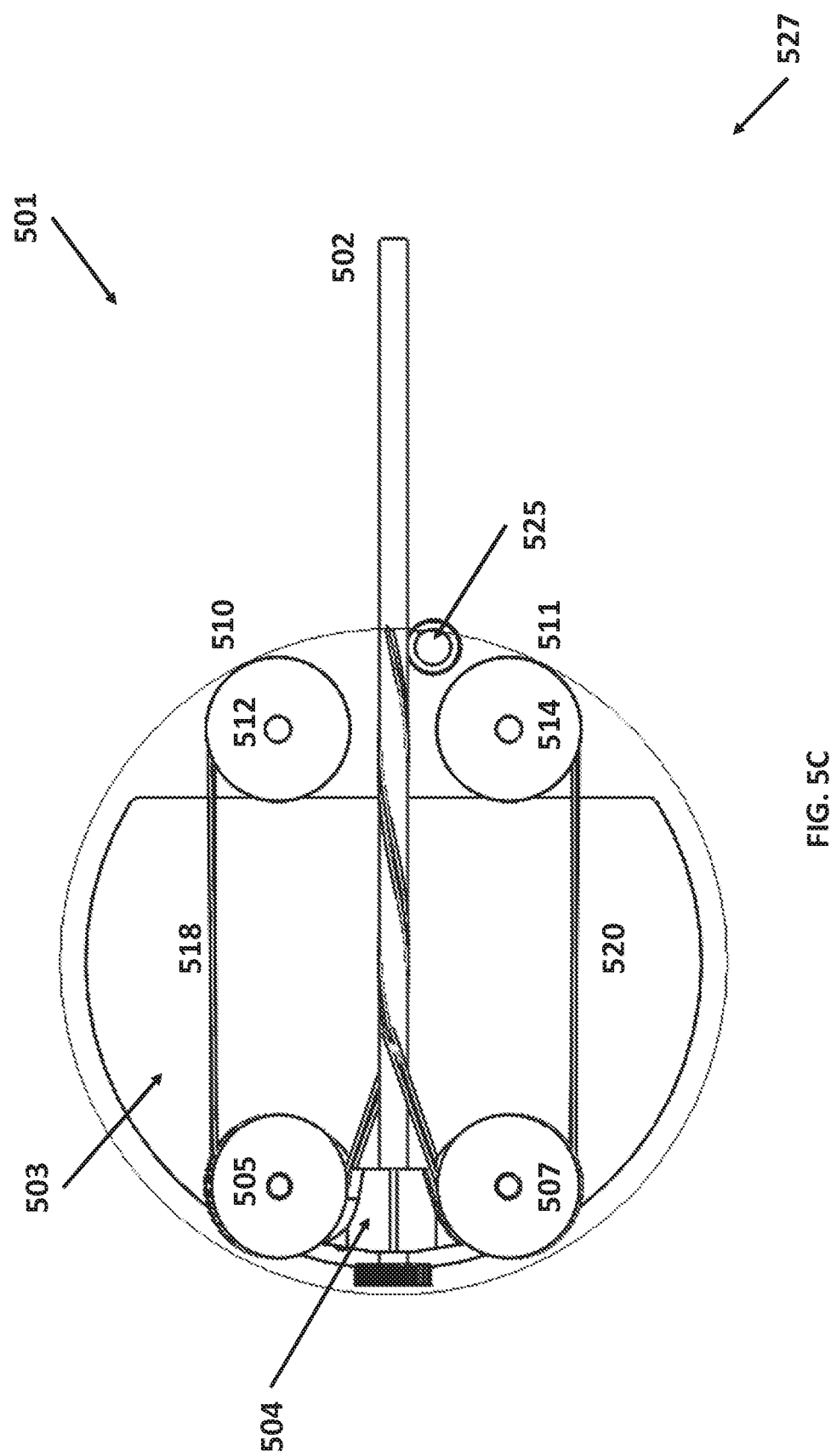
FIG. 5C illustrates a top view that shows the configuration of the key components of endoscopic device 501 from FIG. 5A.

FIG. 5C illustrates a top view that shows the configuration of the key components of endoscopic device 501 from FIG. 5A. Specifically, top view 527 provides a view of the direct alignment of a tangential path between rotation structures 510 and 511 and angled idlers 505 and 507 on idler carriage 504. As shown in top view 527, pull wire 518 is coiled around spool 512 and fed around angled idler 505 before spiraling around elongated shaft 502. The tangential path of the pull wires 518, 520 around the idlers 505, 507 are aligned with the spools 512, 514. Thus, in some embodiments, the spools 513 and 515 are also aligned with the angled idlers 506 and 508 in order for pull wires 519 and 521 to have a direct transmission path between the spools and idlers. In some embodiments, the idlers 505, 506, 507, and 508 may rotate in order to reduce friction as the pull wires 518, 519, 520, and 521 wind around them. While the idlers 505, 506, 507, and 508 operate similar to rotatable spools or pulleys, other embodiments may use other types of redirect members, such as surfaces.

Maintaining a consistent wrapping and unwrapping position and takeoff angle helps ensure that the pull wires spiral around the elongated shaft 502 at a consistent helical pitch. The consistency in the helical pitch greatly increases the ability of the robotic system to control and predict the tension on the pull wires.

In some embodiments, the elongated shaft 502 may be fixedly coupled to a concentric internal shaft that solely resides within the instrument base and is designed for wrapping pull wires around itself. Rolling the internal shaft would effectively roll the elongated shaft while potentially providing other advantages. For example, a distinct internal shaft may be adopted in order to take advantage of different coefficients of friction, different pull wire guiding features, such as grooves or lumens, different diameters, and potentially reduced manufacturing complexity and/or costs.

Angular motion from the robotic interface may create, for example, rotational motion in spool 512 through output shaft 516. Rotational motion in spool 512 may then exert compressive tension in pull wire 518. Tension in pull wire 518 may be carried around angled idler 505 and exerted on the pull wire 518 as it wraps onto elongated shaft 502. Where the pull wires 518 are fixedly coupled to the distal end of the shaft 502, the transmission of the compressive tension along pull wire 518 may then articulate the shaft 502. Thus, the angular motion in the robotic interface may generate articulation in shaft 502.

The instrument base 503 also comprises a lead screw 509 that runs parallel to the elongated shaft 502. Rotation of lead screw 509 is operated by a right angle gear transmission 525, which is visible in isometric view 500 from FIG. 5A. Rotational force in right angle gear transmission 525 originates from lead screw output shaft 526 which interfaces with external robotic drive and control mechanisms. Thus, angular motion in the robotic interface may rotate lead screw output shaft 526 to generate angular motion that ultimately rotates lead screw 509. As with the rotational structures 510 and 511, rotation motion from the robotic interface may also be transmitted to right angle gear transmission 525 using "female" or receiving connectors, rather than lead screw output shaft 526, which is considered a "male" connector.

Figure 5D:
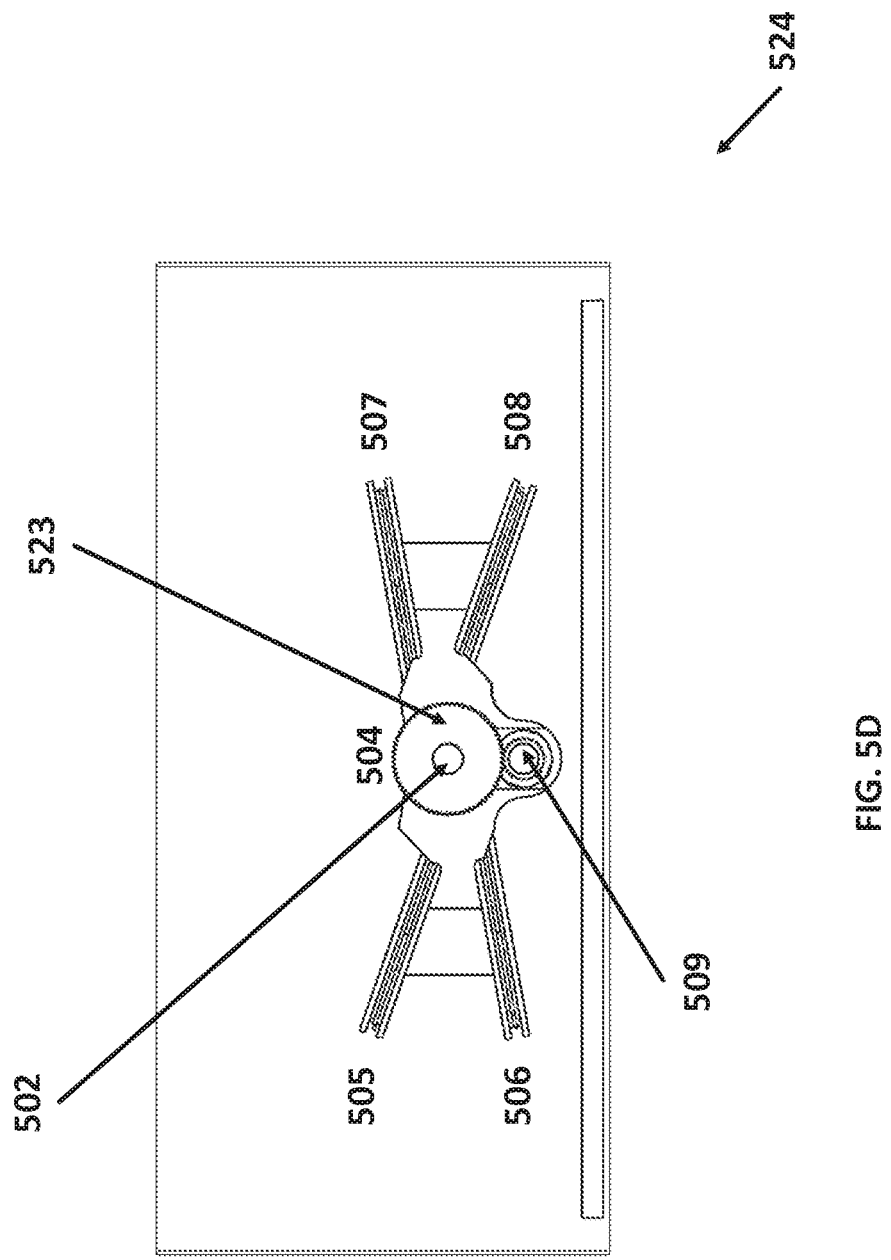
FIG. 5D illustrates a rear view of the elongated shaft idler carriage FIGS. 5A, 5B and 5C.

FIG. 5D illustrates a rear view of the elongated shaft and idler carriage from FIGS. 5A, 5B, and 5C. As shown in rear view 524 from FIG. 5D, lead screw 509 is operatively coupled to elongated shaft 502 through a shaft transmission gear 523. Shaft transmission gear 525 transmits angular motion from the lead screw 509 that rotates the shaft 502. In different embodiments, the shaft transmission gear 523 may be selected from various gear and transmission ratios to ensure the desired rotational motion in the elongated shaft 502 relative to the lead screw 509.

The combination of the shaft 502, lead screw 509, and the idler carriage 504 manages the linear translation of the idler carriage 504 (and thus angled idlers 505, 506, 507, and 508) that helps preserve the helical pitch of the pull wires when rolling of shaft 502. In practice, elongated shaft 502 rotates at a relative speed determined by the angular motion transmitted by shaft transmission gear 523 which is proportional to the rotation of lead screw 509. As the lead screw 509 rotates itself and the elongated shaft 502, the idler carriage 504 acts as a nut on lead screw 509. This "lead screw nut" engagement advances the idler carriage 504 at a rate proportional to the rotation of both the lead screw 509 and elongated shaft 502. Thus, idler carriage 504 translates along the lead screw 509 while sliding freely along the elongated shaft 502 as lead screw 509 rotates itself and elongated shaft 502. The pitch and angle of the thread on lead screw 509 determines the direction and speed at which the idler carriage 504 advances relative to the elongated shaft 502. Similarly, the rate of rotation of elongated shaft 502 is dependent on at least the size of shaft transmission gear 523. Accordingly, careful calibration and selection of those components ensures that they properly coordinate in unison in order to keep consistent the helical pitch and angle of the pull wires about the elongated shaft 502.

Given that the idler carriage 504 translates along the length of the shaft 502 during roll operations, the length and pitch of the lead screw 509 may limit the number of elongated shaft roll revolutions allowed by the device 501. Consequently, longer devices with longer lead screws will generally allow greater shaft roll revolutions than shorter devices with shorter lead screws. Accordingly there may be a longer instrument base 503 to accommodate more rotations from a given lead screw with a specific pitch. Moreover, since wraps around the shaft 502 are directly proportional to the revolutions the shaft 502 may roll, an excessive number of wraps may heavily influence friction. Alternatively, a tighter pitch or steeper angle in the grade of the lead screw 509 may also affect roll revolutions and thus the length of the instrument base.

Figure 6A:
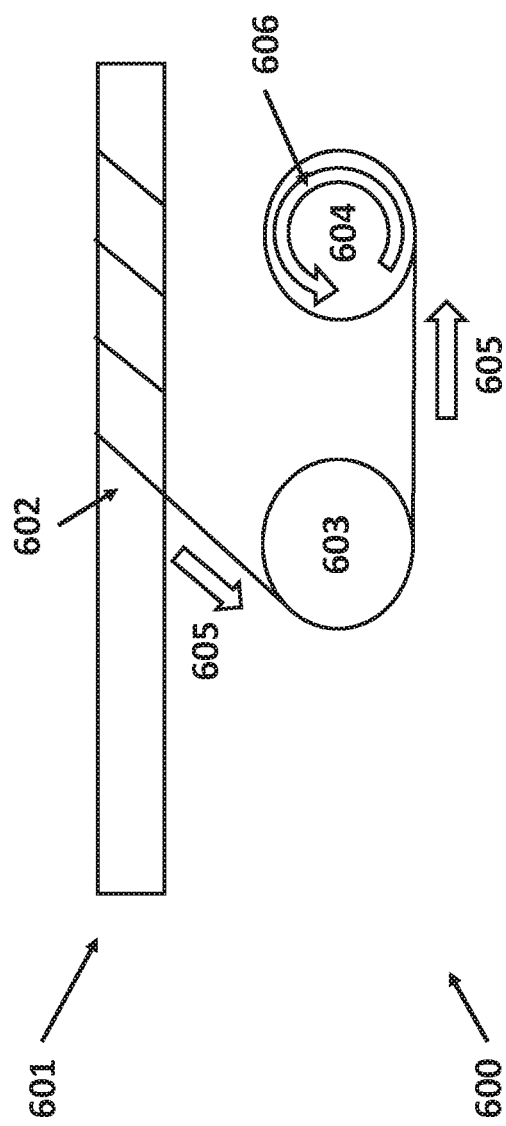
FIG. 6A illustrates how a single pull wire may be tensioned in order to generate articulation in the elongated shaft.
Figure 6B:
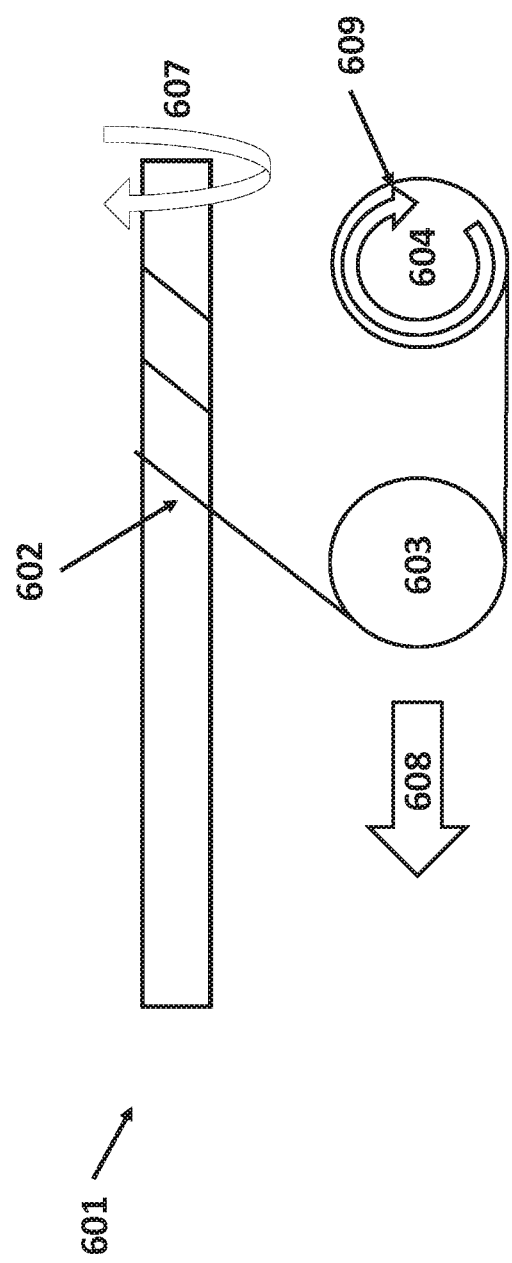
FIG. 6B illustrates how the elongated shaft, pull wire, angled idler, and spool components from FIG. 6A maintain a consistent helical pitch when rolling the elongated shaft clockwise.
Figure 6C:
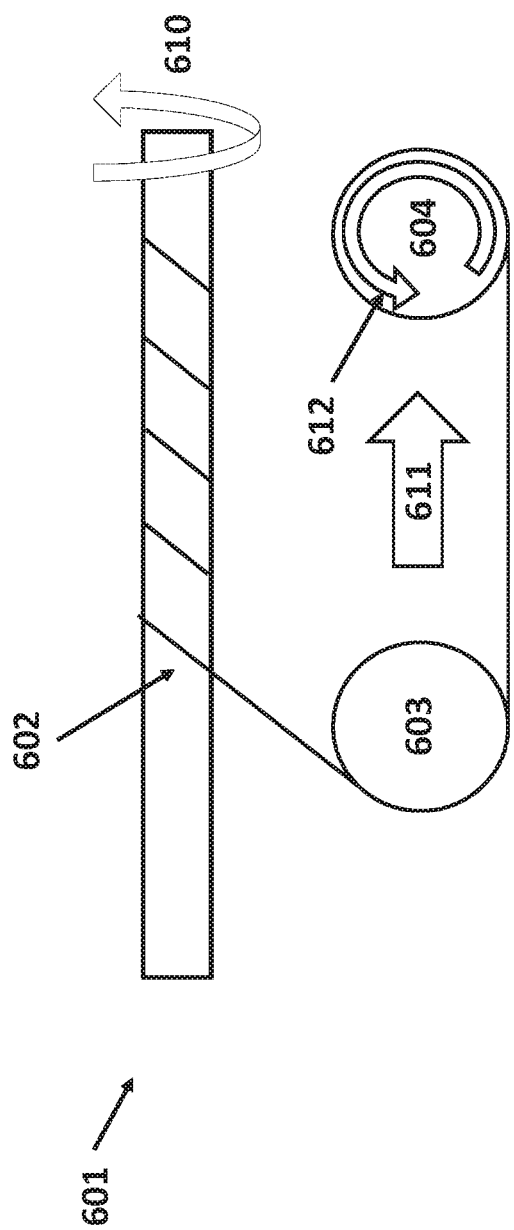
FIG. 6C illustrates how the elongated shaft, pull wire, angled idler, and spool from FIGS. 6A, 6B maintain a consistent helical pitch when rolling the elongated shaft counter-clockwise.

FIGS. 6A-6C illustrates roll and articulation operations of endoscopic device 501 with respect to a single pull wire, single angled idler, and single spool. Specifically, FIG. 6A illustrates how a single pull wire may be tensioned in order to generate articulation in the elongated shaft. As shown in isolated top view 600, exemplar elongated shaft 601 may already be wrapped with a single pull wire 602. Similar to the earlier embodiments, pull wire 602 may be directed to spiral onto a portion of the elongated shaft 601 by angled idler 603. The pull wire 602 may also be controlled via spool 604, whose rotational motion may generate compressive force along the length of the pull wire 602. Thus, in order to tension pull wire 602 and articulate the distal tip of shaft 601, shaft 601 and idler 603 remain static while spool 604 rotates in the direction indicated by arrow 606 to create compression tension along pull wire 602 in the direction indicated by arrow 605. That "pulling" force is then transferred along the length of pull wire around idler 603, along shaft 601 until reaching the distal tip, where the pull wire 602 is fixedly coupled. As the pull wire 602 is fixedly coupled to the end of the distal end of the elongated shaft 601, compressive tension results in bending or articulating of the elongated shaft 601.

FIG. 6B illustrates how the elongated shaft, pull wire, angled idler, and spool components from FIG. 6A maintain a consistent helical pitch when rolling the elongated shaft clockwise. In order to roll the elongated shaft 601, the angled idler 603 may be moved simultaneously to maintain a consistent takeoff angle in the pull wire 602. When rolling the elongated shaft 601 in the clockwise direction indicated by arrow 607, in order to maintain the helical pitch, the angled idler 603 may be translated longitudinally relative to the shaft 601 in the direction indicated by arrow 608. Translating the idler 603 while shaft 601 rotates ensures that the pull wire 602 is wrapped around shaft 601 with a consistent helix by ensuring that the pull wire 602 always has the same takeoff angle from angled idler 603. Put differently, translating the idler 603 in the direction of arrow 608 ensures that the pull wire 602 is "wrapped" around unwrapped portions of the shaft 601 at an even pitch, rather than wrapping in an uneven pitch or even on already-wrapped portions of the shaft 601. Due to the translation of the idler tension in the pull wire 602 requires that the spool 604 be rotated in direction indicated by arrow 609 in order to allow additional length of the pull wire 602 to be wrapped around shaft 601 at a consistent takeoff angle. In effect, the spool 604 must unwrap additional length of the pull wire 602 from itself in order to accommodate the additional wrapping of the pull wire 602 around the shaft 601 and the translation of the idler 603. The rate at which idler 603 advances in direction 608 relative to the rotation of 601 in direction 607 ensures that pull wire 602 is always encounters shaft 601 at the same takeoff angle, which maintains a consistent helical pitch and angle around the shaft 601.

FIG. 6C illustrates how the elongated shaft, pull wire, angled idler, and spool from FIGS. 6A, 6B maintain a consistent helical pitch when rolling the elongated shaft counter-clockwise. When rolling the elongated shaft 601 in the counter-clockwise direction indicated by arrow 610, in order to maintain the helical pitch, the angled idler 603 may be translated longitudinally relative to the shaft 601 in the direction indicated by arrow 611. Translating the idler 603 while shaft 601 rotates ensures that the pull wire 602 has the same takeoff angle as it unwraps from shaft 601. Put differently, translating the idler 603 in the direction of arrow 611 ensures that the pull wire 602 is "unwrapped" with the same takeoff angle from the shaft 601 preserving the helical pitch and angle of the pull wire 602 still wrapped about the shaft 601. Due to the translation of the idler 603, the formation of slack in the pull wire 602 requires that the spool 604 be rotated in direction indicated by arrow 612 in order to collect the loose length of pull wire 602. In effect, the spool 604 must wrap and collect additional length of the pull wire 602 to accommodate the "unwrapping" of the pull wire 602 from the shaft 601 and the translation of the idler 603. The angle of the idler 603 ensures that pull wire 602 is always unwrapped from the shaft 601 at the same point, helping ensure a consistent helical pitch and angle about shaft 601.

The embodiments in FIGS. 5A-5D, 6A-6C enable three-degrees of freedom at the tip of a flexible, articulating device while maintaining a static instrument base (503). By constraining the pull wire helical pitch on the elongated shaft during roll operations, tension variability is minimized and articulation controls are simplified. Furthermore, the design allows for functional adjustments and fine-tuning of features, such as shaft revolutions and relative carriage speed, merely by altering the features of the lead screw and transmission gears. Different configurations of helical wire pitches and the number of revolutions can be attained simply by varying the length of the lead screw, pitch of the threads, and its associated drivetrain to the main shaft. Moreover, the compact design also allows for electronics (such as circuit board 527 in FIG. 5A) and other internal features to be placed within the instrument base.

The embodiments in FIGS. 5A-5D, 6A-6C allow the ability to rotate or "roll" the flexible shaft after a long journey through a tortuous path in the patient's anatomy. For example, after traversing through a long and tortuous path, endoscopic device 501 may articulate elongated shaft 502 and roll elongated shaft 502 in order to reach to an operative site. In some circumstances, it may be useful to first roll elongated shaft 502 and then articulate elongated shaft 502 in order to reach certain locations with the patient's anatomy. Use of roll may also provide improved access to operative sites where robotically-driven articulation may be insufficient and ineffective, a circumstance that may occur as a result of traversing through tortuous paths.

In addition to improved reach, the disclosed embodiments may also enable roll to reduce braking static friction when traversing through a tortuous path. For example, rolling elongated shaft 502 while simultaneously extending into an anatomical lumen may reduce friction caused from contact with the lumen walls. Furthermore, rolling the elongated shaft 502 may also reduce friction caused by contact at anatomical transitions.

In practice, rolling and subsequently articulating endoscopic device 501 within an anatomical lumen involves several mechanical steps. For example, the instrument interface would first rotate lead screw output shaft 526 in order to rotate right angle gear transmission 525. In response to rotating right angle gear transmission 525, lead screw 509 would rotate. The rotation of the lead screw 509 would result in the motion of several components within the instrument base 503. Firstly, the rotation of the lead screw 509 would transmit angular motion to shaft transmission gear 523 which would cause shaft 502 to rotate.

Secondly, rotation of the lead screw 509 would also cause idler carriage 504 to laterally move along the shaft 502. Depending on the direction of rotation and the thread of lead screw 509, the idler carriage 504 may either move forward towards the distal tip of the elongated shaft 502 or back towards the proximal end of the elongated shaft 502.

The roll of elongated shaft 502 creates tension on pull wires 518, 519, 520, 521. To compensate and alleviate the tension, instrument interface would rotate output shafts 516 and 517 (and their associated concentrically-aligned sub-shafts) in order to reduce tension in the pull wires as explained in FIGS. 6B and 6C. Once the roll is complete, the tension-compensation process may terminate. After rotating the shaft 502, the distal tip of the shaft 502 may then be articulated in order to reach the desired operative site. Tensioning the appropriate pull wire in order to articulate may be executed using the technique described in FIG. 6A.

The aforementioned embodiments of the present invention may be designed to interface with robotics platform such as those disclosed in the aforementioned patent applications that are incorporated by reference. For example, the embodiments in FIGS. 5A-5D, 6A-6D may be configured to be driven by an instrument drive mechanism or an instrument device manipulator that is attached to the distal end of a robotic arm through a sterile interface, such as a drape. As part of a larger robotics system, robotic control signals may be communicated from a remotely-located user interface, down the robotic arm, and to the instrument device manipulator to control the instrument or tool.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Elements or components shown with any embodiment herein are exemplary for the specific embodiment and may be used on or in combination with other embodiments disclosed herein. While the invention is susceptible to various modifications and alternative forms, specific examples thereof have been shown in the drawings and are herein described in detail. The invention is not limited, however, to the particular forms or methods disclosed, but to the contrary, covers all modifications, equivalents and alternatives thereof.

What is claimed is:

1. A robotic instrument comprising:
an elongate shaft having a proximal end and a distal end;
an instrument base coupled to the proximal end of the elongate shaft;
a first rotatable body operatively coupled to a first robotic output drive and the elongate shaft such that rotation of the first rotatable body in response to force from the first robotic output drive rotates the elongate shaft; and
a second rotatable body operatively coupled to a second robotic output drive and the elongate shaft such that rotation of the second rotatable body in response to force from the second robotic output drive articulates at least a portion of the elongate shaft,
wherein the second rotatable body comprises two concentrically-aligned spools, and wherein the instrument base is configured to enclose at least a portion of the first rotatable body and at least a portion of the second rotatable body.

2. The robotic instrument of claim 1, wherein the instrument base is configured to enclose the proximal end of the elongate shaft.

3. The robotic instrument of claim 1, further comprising a third rotatable body operatively coupled to the first rotatable body such that rotation of the first rotatable body rotates the third rotatable body.

4. The robotic instrument of claim 3, wherein the elongate shaft is configured to rotate in response to rotation of the third rotatable body.

5. The robotic instrument of claim 3, wherein the third rotatable body comprises a lead screw and the first rotatable body comprises a gear transmission angled with respect to the lead screw.

6. The robotic instrument of claim 3, further comprising a carriage coupled to the proximal end of the elongate shaft, the carriage configured to translate along the length of the elongate shaft.

7. The robotic instrument of claim 6, wherein the carriage comprises a transmission gear to mechanically couple the first rotatable body to the elongate shaft.

8. The robotic instrument of claim 6, wherein the carriage is configured to translate along the elongate shaft as the third rotatable body rotates in response to rotation in the first rotatable body.

9. The robotic instrument of claim 1, further comprising a tendon coupled to the distal end of the elongate shaft and configured to articulate the distal end of the elongate shaft in response to rotation of the second rotatable body.

10. The robotic instrument of claim 9, wherein the tendon is configured to couple to the second robotic output drive through the second rotatable body.

11. The robotic instrument of claim 9, wherein the tendon is a pull wire.

12. The robotic instrument of claim 9, further comprising a carriage that comprises a redirect surface configured to direct the tendon onto the elongate shaft.

13. The robotic instrument of claim 9, further comprising a redirect surface configured to direct the tendon onto the elongate shaft.

14. The robotic instrument of claim 13, wherein the redirect surface comprises of a curved surface.

15. The robotic instrument of claim 13, wherein the redirect surface is configured to direct the tendon onto the elongate shaft at a predetermined angle.

16. The robotic instrument of claim 15, wherein the tendon wraps around the elongate shaft at the same predetermined angle as the elongate shaft rotates.

17. The robotic instrument of claim 15, wherein the predetermined angle comprises a predetermined helical angle and pitch.

18. A method of operating a robotic instrument, the method comprising:

providing a robotic instrument comprising an elongate shaft, an instrument base coupled to a proximal end of the elongate shaft, a first rotatable body, and a second rotatable body;

coupling the first rotatable body to a first robotic drive output;

rotating, with the first robotic drive output, the first rotatable body to rotate the elongate shaft of the robotic instrument;

coupling the second rotatable body to a second robotic drive output; and rotating, with the second robotic drive output, the second rotatable body to articulate at least a portion of the elongate shaft of the robotic instrument, wherein the second rotatable body comprises two concentrically-aligned spools, and wherein the instrument base is configured to enclose at least a portion of the first rotatable body and at least a portion of the second rotatable body.

19. The method of claim 18, wherein rotating, with the first robotic drive output, the first rotatable body to rotate the elongate shaft comprises operatively coupling a third rotatable body to the first rotatable body, rotating the third rotatable body in response to rotation of the first rotatable body, and operatively coupling the third rotatable body to the elongate shaft.

20. The method of claim 19, wherein third rotatable body comprises a lead screw and the first rotatable body comprises a gear transmission angled with respect to the lead screw.

21. The method of claim 20, further comprising translating a carriage along the elongate shaft in response to rotation of the third rotatable body.

22. The method of claim 21, wherein rotating the second rotatable body to articulate at least a portion of the elongate shaft comprises tensioning a tendon coupled to the elongate shaft.

23. The method of claim 22, wherein the tendon is a pull wire.

24. The method of claim 22, wherein the tendon is directed onto the elongate shaft around a redirect surface.

25. The method of claim 24, wherein the redirect surface comprises of a curved surface.

26. The method of claim 22, further comprising maintaining a predetermined angle of the tendon with respect to the elongate shaft as the elongate shaft rotates or the tendon is tensioned.

27. The method of claim 26, wherein the predetermined angle comprises a predetermined helical angle and pitch.

28. The method of claim 26, wherein maintaining the predetermined angle comprises translating the carriage along the elongate shaft, the carriage being coupled to the tendon.

29. The method of claim 28, wherein the carriage comprises of a redirect surface configured to direct the tendon onto the elongate shaft at the predetermined angle.

* * * * *